United States Patent [19]

Eibofner

[11] 4,281,988
[45] Aug. 4, 1981

[54] DENTAL HANDPIECE

[75] Inventor: Eugen Eibofner, Biberach, Fed. Rep. of Germany

[73] Assignee: Kaltenbach & Voight GmbH & Co., Fed. Rep. of Germany

[21] Appl. No.: 56,000

[22] Filed: Jul. 9, 1979

[30] Foreign Application Priority Data

Jul. 21, 1978 [DE] Fed. Rep. of Germany ....... 2832157

[51] Int. Cl.³ .............................................. A61C 1/14
[52] U.S. Cl. .................................................. 433/129
[58] Field of Search ..................... 433/127, 129; 279/7, 279/36, 46–54

[56] References Cited

U.S. PATENT DOCUMENTS

| | | | |
|---|---|---|---|
| 1,114,653 | 10/1914 | Starin | 279/52 |
| 2,778,650 | 1/1957 | Benjamin et al. | 279/46 |
| 3,962,788 | 6/1976 | Flatland | 433/129 |

*Primary Examiner*—Robert Peshock
*Attorney, Agent, or Firm*—Scully, Scott, Murphy & Presser

[57] ABSTRACT

A dental handpiece includes a drive shaft rotatably supported interiorly thereof, the drive shaft being hollow at least at the operating end thereof and having an internal thread; and a tubular friction collet in the hollow space having an external thread end evidencing in the inoperative condition thereof inwardly bent resilient tongues formed by a plurality of slits for the receipt and gripping of the shaft of an implement. The external thread of the friction collet is arranged at the implement-sided end thereof as in a threaded collet, the friction collet having an external conical surface and the hollow drive shaft having an internal conical surface cooperating with the external conical surface.

6 Claims, 3 Drawing Figures

DENTAL HANDPIECE

BACKGROUND OF THE INVENTION

1. Field of the Invention

The present invention relates to a dental handpiece including a drive shaft rotatably supported interiorly thereof, which is constructed hollow at least at its operating end and is provided with an internal thread, and wherein there is located in the thus formed hollow space a tubular friction collet which is provided with an external thread and evidencing in the inoperative condition thereof inwardly bent resilient tongues formed by a plurality of slits for the receipt and the gripping of the shaft of an implement which is detachably insertable from externally thereof.

The implement can be formed by a drill, grinding or polishing tool, or the like.

2. Discussion of the Prior Art

A handpiece of that type has become known from German Patent No. 10 84 869. In this known handpiece, the external thread of the friction collet is arranged on the collet and proximate the implement and, in a similar manner, the internal thread of the hollow drive shaft is arranged on the shaft end proximate the implement whereby the tongues which are formed by the axially parallel extending slits extending to the end of the collet are located on the end of the collet remote from the implement. In order that at the insertion of the collet into the hollow drive shaft from the end of the hollow drive shaft proximate the implement, the unthreaded portion of the collet can slide unhindered past the internal thread of the drive shaft bounds are set on the outer diameter of the unthreaded collet portion so that an annular gap is formed between the last mentioned and the inner wall of the hollow drive shaft. This annular gap is thus elatively narrow, however, the thereby produced small tolerance is adequate, particularly at radially acting implement loads, to offset a tipping of the implement about an imaginary axis which extends radially in the region of the engagement of the threads which, during operation with the handpiece, will lead to an oscillating and knocking of the implement shaft located within the hollow drive shaft and, as a result, to the deformation of the shaft or the wall structure of the hollow space of the drive shaft. This will extensively and adversely influence any dental treatment. Through the continual knocking of the implement shaft, this can finally lead to the destruction of the drive shaft. In addition thereto, the clamping force of the resilient tongues of this known friction collet, in any event in the built-in condition, cannot be adjusted.

The mentioned knocking or hammering can be reduced in a handpiece as has become known from German Published Patent Application No. 19 27 743, since the collet inserted without threading into the hollow drive shaft evidences end regions which are unslitted and cylindrically-shaped, and which is retained in the collet by a special guide sleeve inserted with a press fit at each end of the collet. The inwardly bent gripping tongues are arranged in the region intermediate the cylindrically constructed end regions. The guide sleeves, as special components, represent an energy absorbent weight increase; moreover, in case of need the guide sleeves render more difficult a rapid exchange of the collet since it can mostly be disassembled and reassembled in operating with only the aid of specialized disengaging and clamping arrangements.

From German Published Patent Application No. 12 68 311 there has become known a dental handpiece which is similar to the above-mentioned handpiece, however, with the distinction that no friction collet but a threaded collet is screwed into the hollow space of the drive shaft, in essence a collet whose tongues are not inwardly bent in the inoperative condition, in effect, not prestressed. The external thread of this threaded collet is located on the end of the last-mentioned collet remote from the implement whereby the collet evidences an external conical surface cooperating with an internal conical surface of the hollow drive shaft.

Through the mutual screwing together of the collet and the drive shaft under the utilization of a key, the collet and the drive shaft are longitudinally displaced relative to each whereby, through the interaction of the internal conical surface and the external conical surface, the tongues of the collet come into gripping contact with the implement shaft and restrain the last-mentioned within the hollow drive shaft.

A handpiece with a friction collet which has become known from the above-mentioned German Patent No. 10 84 869 has the advantage that the implement shaft, upon occasion with the assistance of special pressure or thrust tools, can be withdrawn relatively rapidly from the collet grip and inserted therein. The handpiece with the threaded collet which is known from the above-mentioned German Published Patent Application No. 12 68 311 affords the advantage that through a suitably strong tightening of the threads there can be achieved an extremely rigid seating of the implement shaft.

There is thus present the requirement for the dentist that, in accordance with the kind of treatment which is to be effected, there be employed either a friction collet or a threaded collet. Heretofore, two different handpieces were required for this purpose.

SUMMARY OF THE INVENTION

Accordingly, it is an object of the present invention to provide a novel and unique dental handpiece of the above-mentioned type wherein the contemplated advantages can be selectively employed through the use of, on the one hand, friction collets and, on the other hand, threaded collets, and namely with the avoidance of the deleterious knocking, as well as the need for an arrangement of specialized guide sleeves which are difficult to insert and remove.

The advantages which are attained through the invention can be essentially ascertained in that the dentist, if he now prefers a rapid exchange of the implement or a particularly rapid seating of the implement, can with one and the same handpiece selectively employ either a friction collet or a threaded collet. Pursuant to the invention the handpiece is essentially constructed in such a manner that there can be arranged therein either a friction collet or a threaded collet whereby the dentist only needs to remove the collet present in the handpiece, for example, a friction collet unscrewed with the use of a key and to then screw in a threaded collet while employing the same key. This will impart an advantage in that this single key can be employed not only for the mentioned collet exchange, but also for the implement exchange with a threaded collet, for example, for the tightening of the threaded collet. Finally, the mentioned single key can also find utilization for a screwed-in friction collet, for example, in case of fatigueing of the inwardly bent resilient gripping tongues for the adjustment of the gripping tongues with a predetermined range since in this instance, due to the cooperation between the internal conical surface of the hollow drive shaft and the external conical surface of the friction collet, during the tightening of the threads a predetermined radial pressure as viewed in the axial direction of the tubularly-shaped friction collet, can be exerted on the gripping tongues most closely to the outer conical surface end of the collet.

A further advantage consists of in that the already achievable secure seating of the inserted implement shaft for threaded collets is also attainable through the proposed construction for a friction collet inserted in the handpiece, since the unslitted end region supporting the external thread and the similarly unslitted end region of the collet which supports the external conical surface form a secure guidance for the implement shaft.

Further embodiments of the invention may now be ascertained from the following detailed description thereof, taken in conjunction with the accompanying drawings; in which.

DETAILED INFORMATION

Figure 1:
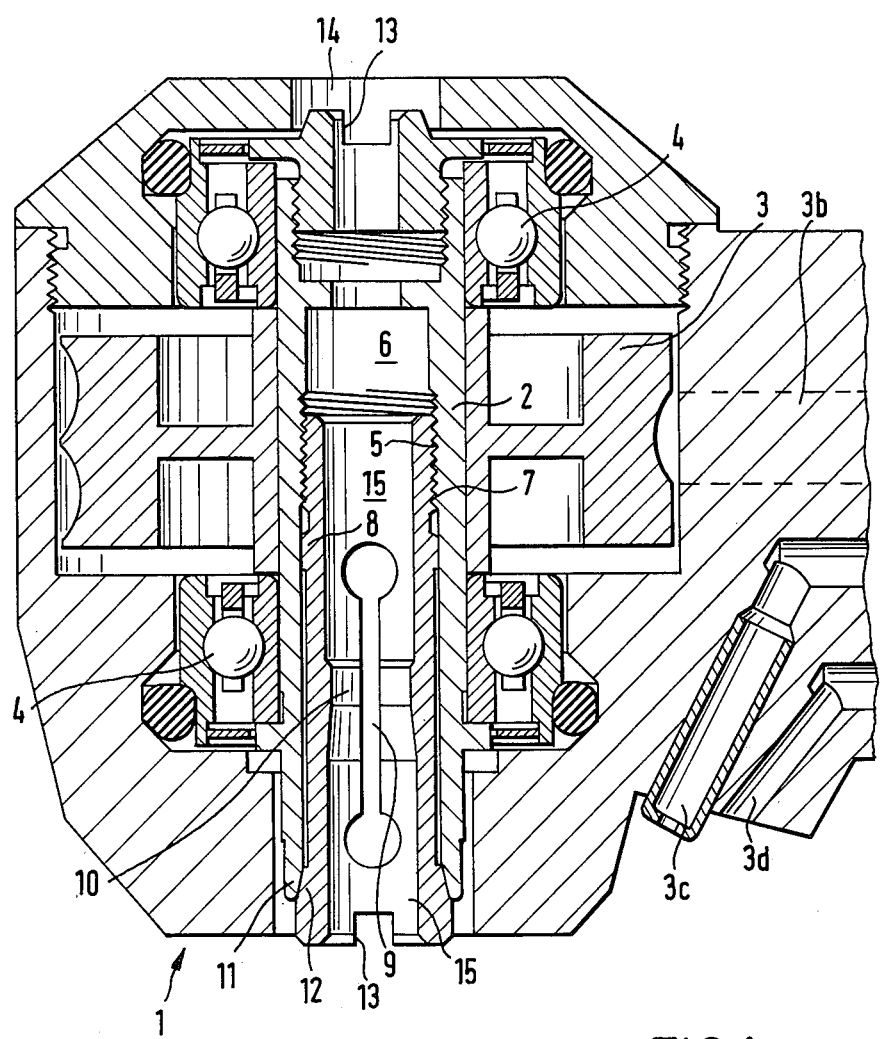
FIG. 1 illustrates a sectional view through an angled headpiece of a dental handpiece formed as a turbine-angle member with a friction collet inserted into the hollow drive shaft.
Figure 3:
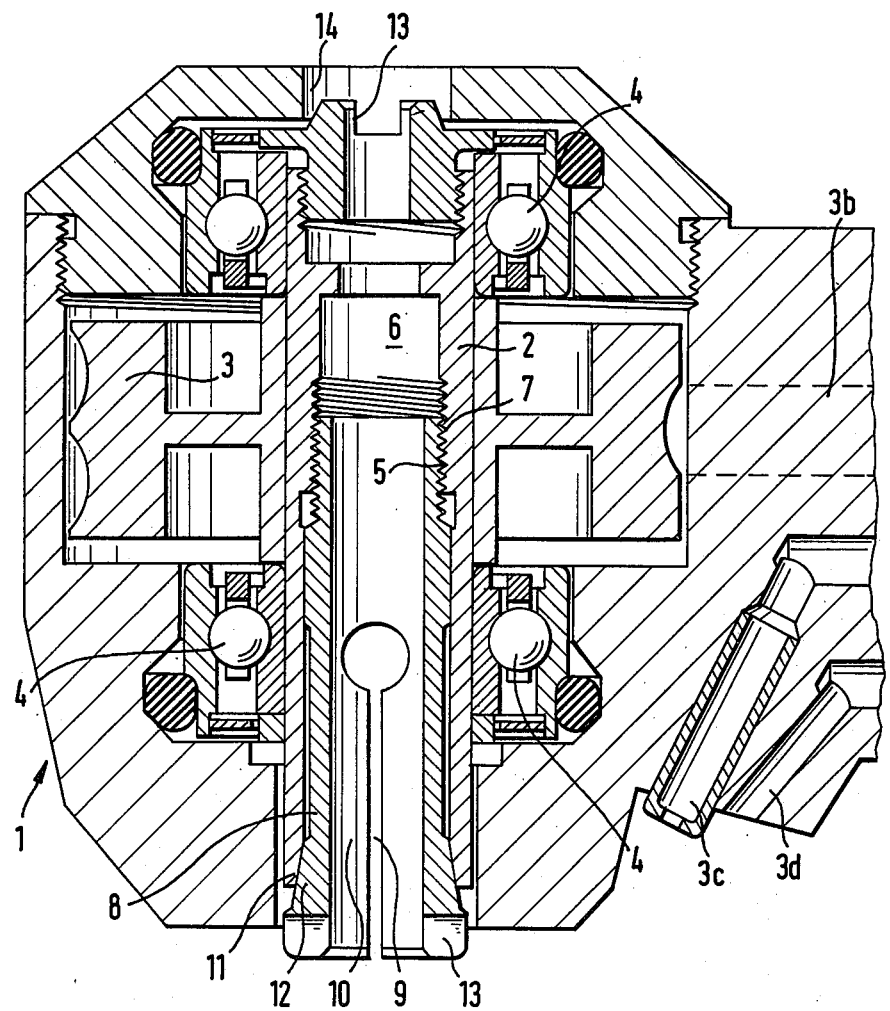
FIG. 3 illustrates an angle headpiece according to FIG. 1 with a threaded collet inserted into the hollow drive shaft.

The dental handpiece illustrated in FIGS. 1 and 3 of the drawings relates to an angled turbine member. Supported in angled head piece 1 of this angled turbine member a hollow drive shaft 2 which is formed by the turbine rotor shaft. The turbine blades are identified by reference numeral 3. The turbine blades 3 are subjected to pressurized air. For this purpose a pressurized air infeed conduit 3b is provided in the handpiece. The conduits 3c and 3d relates, respectively, to inlet conduits for water and pressurized air for the formation of a spray, so as to in this manner cool an inplement inserted in the collet 8 described hereinbelow. The supports for the hollow drive shaft 2 are formed by ball bearings 4.

The hollow drive shaft 2 is provided with an internal thread 5. Threaded into the hollow space 6 of the hollow drive shaft 2 is a collet 8, which is provided with an external thread 7, wherein the two threads 5 and 7 are engaged with each other. The collet 8 is tubularly-shaped and possesses resilient tongues 10 formed through the intermediary of a plurality of axially parallel slits 9.

Figure 2:
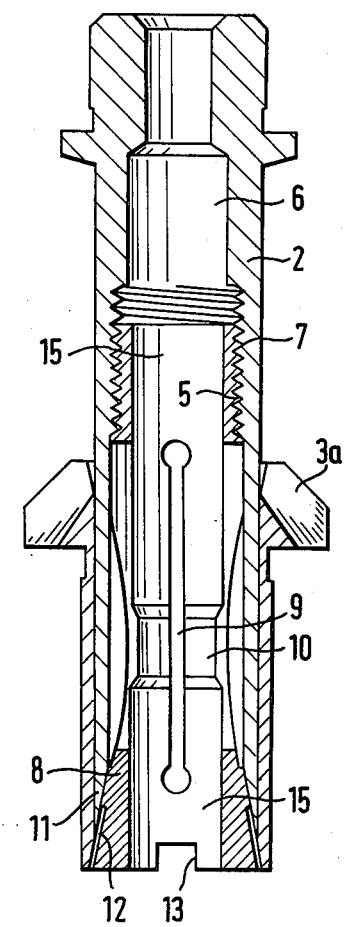
FIG. 2 illustrates a hollow drive shaft with a friction collet inserted therein having modified construction in contrast with that in FIG. 1.

In the embodiments pursuant to FIGS. 1 and 2, the collet 8 is formed by a friction collet. Such a friction collet distinguishes itself in that the resilient tongues 10 in the inoperative condition, in essence, at a not inserted implement shaft, are bent inwardly and are hereby prestressed.

As can be ascertained from FIGS. 1 and 2, in accordance with the type of a screw collet, the external thread 7 of the friction collet 8 is arranged at the end of the collet which is distant from the implement. The friction collet further possesses an external conical surface 12 cooperating with an internal conical surface 11 of the hollow drive shaft 2. The internal thread 5 of the hollow drive shaft 2 is located at a distance from the implement-sided end of the drive shaft 2 approximately conforming to the length of the unthreaded portion of the collet 8.

The internal conical surface 11 of the hollow drive shaft 2 widens in the end region proximate the implement towards the size of the shaft end, and the external conical surface 12 of the collet 8 similarly widens at the implement-sided end to the size of the collet end 2.

Provided at the end of the hollow drive shaft 2 distant from the implement and at the end of the collet 8 proximate the implement are key flats or recesses 13 for the application of a known per se key for the easy screwing together and screwing apart of the drive shaft 2 and the collet 8. These key surfaces or recesses 13 are arranged in access apertures 14 formed in the handpiece for the through passage of the key. In accordance with FIGS. 1 and 3, these access apertures 14 are located on the surface of the angled headpiece 1 and essentially for access to the key surfaces or recesses 13 of the drive shaft 2. The lower key surfaces or recesses 13 of the collet 8 are accessible without hindrance.

As illustrated in FIGS. 1 and 2, the friction collet 8 possesses unslitted end regions 15. The resilient tongues 10 which are formed by the axially parallel slits 9 are hereby arranged in the region intermediate the two unslotted end regions 15.

The one end region of the collet and in essence the lower unslotted end region 15 of the friction collet 8, is equipped with the external conical surface 12 and the other unslotted end region 15 with the external thread 7.

In the embodiment pursuant to FIG. 2 the details with regard to the hollow drive shaft 2 and friction collet 8 are essentially coincident. However, in this instance, in lieu of turbine blades 3 there is provided a drive gear 3a.

The illustrated construction has the advantage that the dentist can selectively employ with one and the same handpiece either a friction collet or a threaded collet. For this purpose, he needs to only unscrew the friction collet 8 as shown in FIG. 1 from the hollow drive shaft 2, and to screw in a threaded collet 8, as illustrated in FIG. 3, into the hollow drive shaft. A threaded collet differs essentially from a friction collet in that the gripping tongues 10 are not inwardly bent, even in the inoperative condition. The axially parallel slots 9 of the threaded collet 8 illustrated in FIG. 3 which form the tongues 10 are located at the end of the collet proximate the implement, in effect, they emanate from that end and extend to about the middle of the length of the threaded collet 8.

Although the invention is illustrated only with regard to exemplary embodiments in the form of angled dental pieces, they can also be utilized in linear handpieces, such as is illustrated, for example, in FIGS. 5 and 6 of German Pat. No. 17 66 823.

What is claimed is:

1. In a dental handpiece including a drive shaft rotatably supported interiorly thereof, said drive shaft being hollow at least at the operating end thereof and having an internal thread; and a tubular friction collet in the hollow space, having an external thread and evidencing in the inoperative condition thereof inwardly bent resilient tongues formed by a plurality of slits for the receipt and gripping of the shaft of an implement; the improvement comprising: the external thread of said friction collet being arranged at the implement-sided end thereof as in a threaded collet, said friction collet having an external conical surface and said hollow drive shaft an internal conical surface cooperating with said external conical surface, and wherein the internal conical surface of said hollow drive shaft widens to the shaft end at the implement-sided end region thereof, and the external conical surface of the friction collet widens at the implement-sided end region thereof towards that end of said collet.

2. Dental handpiece as claimed in claim 1, the internal thread of the hollow drive shaft being arranged at a distance from the implement-sided end of said drive shaft corresponding substantially to the length of the unthreaded portion of said collet.

3. Dental handpiece as claimed in claim 1, comprising key surfaces being arranged on the end of said hollow drive shaft remote from the implement end on the end of said friction collet proximate the implement.

4. Dental handpiece as claimed in claim 1, comprising key recesses being arranged in the end of said hollow drive shaft remote from the implement end in the end of said friction collet proximate the implement.

5. Dental handpiece as claimed in claim 3 or 4, comprising accessibility apertures in said handpiece being associated with said key, surfaces and recesses for the through passage of a key.

6. Dental handpiece as claimed in claim 1, said friction collet having unslitted end regions, said inwardly bent resilient tongues formed by axially parallel slits being located in the region intermediate said unslitted end regions.

* * * * *